US008377885B2

(12) United States Patent
Marom et al.

(10) Patent No.: US 8,377,885 B2
(45) Date of Patent: *Feb. 19, 2013

(54) DEPOT SYSTEMS COMPRISING GLATIRAMER OR PHARMACOLOGICALLY ACCEPTABLE SALT THEREOF

(75) Inventors: Ehud Marom, Kfar Saba (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,472

(22) Filed: Feb. 29, 2012

(65) Prior Publication Data

US 2012/0164229 A1 Jun. 28, 2012

Related U.S. Application Data

(63) Continuation-in-part of application No. 13/258,808, filed as application No. PCT/IL2010/000679 on Aug. 19, 2010.

(60) Provisional application No. 61/291,928, filed on Jan. 4, 2010.

(51) Int. Cl.
| | |
|---|---|
| A61K 38/16 | (2006.01) |
| A61K 38/10 | (2006.01) |
| A61K 38/02 | (2006.01) |
| A61K 9/14 | (2006.01) |
| C07K 2/00 | (2006.01) |
| C07K 7/08 | (2006.01) |
| C07K 14/00 | (2006.01) |
| A61P 25/00 | (2006.01) |
| A61P 37/04 | (2006.01) |

(52) U.S. Cl. ...... 514/17.9; 514/1.1; 514/21.3; 514/21.4; 514/21.5; 530/300; 530/324; 530/325; 424/457; 424/489

(58) Field of Classification Search .................. None
See application file for complete search history.

(56) References Cited

U.S. PATENT DOCUMENTS

| | | | |
|---|---|---|---|
| 3,773,919 | A | 11/1973 | Boswell |
| 3,849,550 | A | 11/1974 | Teitelbaum |
| 5,800,808 | A | 9/1998 | Konfino |
| 5,858,964 | A | 1/1999 | Aharoni |
| 5,981,589 | A | 11/1999 | Konfino |
| 6,048,898 | A | 4/2000 | Konfino |
| 6,054,430 | A | 4/2000 | Konfino |
| 6,214,791 | B1 | 4/2001 | Arnon |
| 6,342,476 | B1 | 1/2002 | Konfino |
| 6,362,161 | B1 | 3/2002 | Konfino |
| 6,620,847 | B2 | 9/2003 | Konfino |
| 6,835,711 | B2 | 12/2004 | Eisenbach-Schwartz |
| 6,844,314 | B2 | 1/2005 | Eisenbach-Schwartz |
| 6,939,539 | B2 | 9/2005 | Konfino |
| 7,199,098 | B2 | 4/2007 | Konfino |
| 7,381,790 | B2 | 6/2008 | Strominger |
| 7,655,221 | B2 | 2/2010 | Rasmussen |
| 2006/0276390 | A1* | 12/2006 | Aharoni et al. ................. 514/12 |
| 2008/0063687 | A1 | 3/2008 | Chou |
| 2008/0194462 | A1 | 8/2008 | Wucherpfennig |
| 2010/0298227 | A1 | 11/2010 | Aharoni |
| 2012/0015891 | A1 | 1/2012 | Marom |

FOREIGN PATENT DOCUMENTS

| | | |
|---|---|---|
| WO | 95/31990 | 11/1995 |
| WO | 00/05250 | 2/2000 |
| WO | 00/27417 | 5/2000 |
| WO | 01/52878 | 7/2001 |
| WO | 01/93893 | 12/2001 |
| WO | 2008/075365 | 6/2008 |

OTHER PUBLICATIONS

Shenoy DB, D'Souza RJ, Udupa N, "Poly(DL-lactide-co-glycolide) microporous microsphere-based depot formulation of a peptide-like antineoplastic agent," Journal of Microencapsulation, 2002, 19(4): 523-535.*
Abramsky, O. et. al., (1982) Alpha-fetoprotein suppresses experimental allergic encephalomyelitis. J Neuroimmunol 2(1):1-7.
Aharoni, Rina et al., (1998) Bystander suppression of experimental autoimmune encephalomyelitis by T cell lines and clones of the Th2 type induced by copolymer 1. J Neuroimmunol 91(1-2):135-146.
Aharoni, Rina et al., (2005) The immunomodulator glatiramer acetate augments the expression of neurotrophic factors in brains of experimental autoimmune encephalomyelitis mice. Proc Natl Acad Sci USA 102(52):19045-19050.
Ben-Nun, Avraham et al., (1996) The autoimmune reactivity to myelin oligodendrocyte glycoprotein (MOG) in multiple sclerosis is potentially pathogenic: effect of copolymer 1 on MOG-induced disease. J Neurol 243(Suppl 1):S14-S22.
Bolton, C. et al., (1982) Immunosuppression by cyclosporin A of experimental allergic encephalomyelitis. J Neurol Sci 56:147-153.
Bright, John J. et al., (1999) Tyrphostin B42 inhibits IL-12-induced tyrosine phosphorylation and activation of Janus kinase-2 and prevents experimental allergic encephalomyelitis. J Immunol 162:6255-6262.
Cohen, J. A. et al., (2007) Randomized, double-blind, dose-comparison study of glatiramer acetate in relapsing-remitting MS. Neurology 68:939-944.
Fridkis-Hareli, Masha et al., (1999) Binding of random copolymers of three amino acids to class II MHC molecules. Int. Immunol. 11(5):635-641. Johnson, K. P. et al., (1995) Copolymer 1 reduces relapse rate and improves disability in relapsing—remitting multiple sclerosis.Results of a phase III multicenter, double—blind, placebo—controlled trial. Neurology 45 (7):1268-1276.
Shenoy, D. B. et al., (2002) Poly(DL-lactide-co-glycolide) microporous microsphere-based depot formulation of a peptide-like antineoplastic agent. J Microencapsul 19(4):523-535.
Sorensen, P. S. et al., (1998) Intravenous immunoglobulin G reduces MRI activity in relapsing multiple sclerosis. Neurology 50(5):1273-1281.

(Continued)

Primary Examiner — Julie Ha
(74) Attorney, Agent, or Firm — Rothwell, Figg, Ernst & Manbeck, P.C.

(57) ABSTRACT

Long acting parenteral pharmaceutical compositions comprising a therapeutically effective amount of glatiramer are provided. In particular, the present invention provides a long acting pharmaceutical composition comprising a therapeutically effective amount of glatiramer acetate in depot form suitable for administering at a medically acceptable location in a subject in need thereof. The depot form is suitable for subcutaneous or intramuscular implantation or injection.

26 Claims, 9 Drawing Sheets

OTHER PUBLICATIONS

Stern, Joel N. et al., (2008) Amino acid copolymer-specific IL-10-secreting regulatory T cells that ameliorate autoimmune diseases in mice. Proc Natl Acad Sci USA 105(13):5172-5176.

Teitelbaum, Dvora et al., (1971) Suppression of experimental allergic encephalomyelitis by a synthetic polypeptide. Eur J Immunol 1(4):242-248.

Teitelbaum, Dvora et al., (1973) Suppression by several synthetic polypeptides of experimental allergic encephalomyelitis induced in guinea pigs and rabbits with bovine and human basic encephalitogen. Eur J Immunol 3 (5):273-279.

Teitelbaum, Dvora et al., (1974) Suppression of experimental allergic encephalomyelitis in rhesus monkeys by a synthetic basic copolymer. Clin. Immunol. Immunopathol. 3(2):256-262.

Teitelbaum, Dvora et al., (1996) Copolymer 1 inhibits chronic relapsing experimental allergic encephalomyelitis induced by proteolipid protein (PLP) peptides in mice and interferes with PLP-specific T cell responses. J Neuroimmunol 64(2):209-217.

Webb, Cynthia et al., (1973) Correlation between strain differences in susceptibility to experimental allergic encephalomyelitis and the immune response to encephalitogenic protein in inbred guinea pigs. Immunol Commun. 2 (2):185-192.

ISR of PCT/IL2010/000679 mailed Dec. 27, 2010.

ISR of PCT/IL2012/050138 mailed Aug. 31, 2012.

Armstrong, Joseph D. et al., (1997) A Novel Synthesis of Disubstituted Ureas Using Titanium(IV) Isopropoxide and Sodium Borohydride. Tetrahedron Letters 36(9): 1531-1532.

Artuso, Emma et al., (2007) Preparation of Mono-, Di-, and Trisubstituted Ureas by Carbonylation of Aliphatic Amines with S,S-Dimethyl Dithiocarbonate. Synthesis 22: 3497-3506.

* cited by examiner

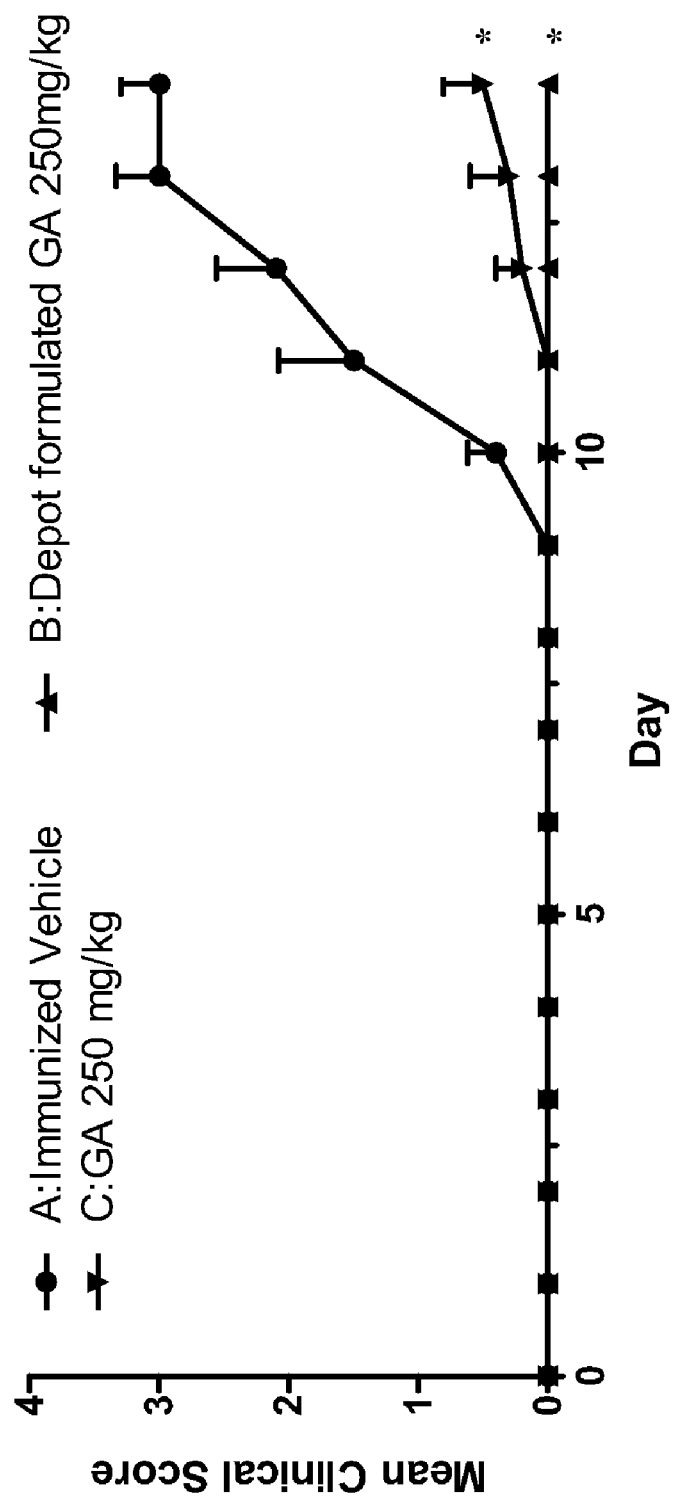

DEPOT SYSTEMS COMPRISING GLATIRAMER OR PHARMACOLOGICALLY ACCEPTABLE SALT THEREOF

CROSS REFERENCE TO RELATED APPLICATIONS

The present application is a Continuation-In-Part of U.S. patent application Ser. No. 13/258,808, filed on Sep. 22, 2011, which is a 35 U.S.C. §371 National Phase Entry Application from PCT/IL2010/000679, filed Aug. 19, 2010, and designating the United States, which claims the benefit of U.S. Provisional Application No. 61/291,928, filed Jan. 4, 2010, the disclosure of which is incorporated herein in its entirety by reference.

FIELD OF THE INVENTION

The present invention relates to long acting dosage forms of glatiramer acetate and other pharmacologically acceptable salts of glatiramer. Particularly preferred are depot systems and other implantable systems for prolonged release of glatiramer acetate.

BACKGROUND OF THE INVENTION

Glatiramer Acetate

Copolymer-1, also known as glatiramer acetate and marketed under the tradename Copaxone®, comprises the acetate salts of polypeptides containing L-glutamic acid, L-alanine, L-tyrosine and L-lysine. The average molar fractions of the amino acids are 0.141, 0.427, 0.095 and 0.338, respectively, and the average molecular weight of copolymer-1 is between 4,700 and 11,000 daltons. Chemically, glatiramer acetate is designated L-glutamic acid polymer with L-alanine, L-lysine and L-tyrosine, acetate (salt). Its structural formula is:

(Glu, Ala, Lys, Tyr)$x$CH$_3$COOH (C$_5$H$_9$NO$_4$—
  C$_3$H$_7$NO$_2$_C$_6$H$_{14}$N$_2$O$_2$_C$_9$H$_{11}$NO$_3$)$x$C$_2$H$_4$O$_2$
  [CAS—147245-92-9], approx. ratio Glu$_{14}$Ala$_{43}$Tyr$_{10}$Lyz$_{34}$$x$(CH$_3$COOH)$_{20}$. Copaxone® is a clear, colorless to slightly yellow, sterile, nonpyrogenic solution for subcutaneous injection. Each milliliter contains 20 mg of glatiramer acetate and 40 mg of mannitol. The pH range of the solution is approximately 5.5 to 7.0.

Mechanism of Action

Glatiramer acetate is a random polymer (average molecular mass 6.4 kD) composed of four amino acids that are found in myelin basic protein. The mechanism of action for glatiramer acetate is unknown, although some important immunological properties of this copolymer have emerged. Administration of copolymer-1 shifts the population of T cells from pro-inflammatory Th1 cells to regulatory Th2 cells that suppress the inflammatory response (FDA Copaxone® label). Given its resemblance to myelin basic protein, copolymer-1 may also act as a decoy, diverting an autoimmune response against myelin. The integrity of the blood-brain barrier, however, is not appreciably affected by copolymer-1, at least not in the early stages of treatment.

Copolymer-1 is a non-autoantigen which has been demonstrated to suppress experimental allergic encephalomyelitis (EAE) induced by various encephalitogens including mouse spinal cord homogenate (MSCH) which includes all myelin antigens, such as myelin basic protein (MBP) (Sela M et al., Bull Inst Pasteur (1990) 88 303-314), proteolipid protein (PLP) (Teitelbaum D et al., J Neuroimmunol (1996) 64 209-217) and myelin oligodendrocyte glycoprotein (MOG) (Ben-Nun A et al., J Neurol (1996) 243 (Suppl 1) S14-S22) in a variety of species. EAE is an accepted model for multiple sclerosis.

Copolymer-1 has been demonstrated to be active when injected subcutaneously, intraperitoneally, intravenously or intramuscularly (Teitelbaum D et al., Eur J Immunol (1971) 1 242-248; Teitelbaum D et al., Eur J Immunol (1973) 3 273-279). In phase III clinical trials, daily subcutaneous injections of copolymer-1 were found to slow the progression of disability and reduce the relapse rate in exacerbating-remitting multiple sclerosis (Johnson K P, Neurology (1995) 1 65-70; www.copaxone.com). Copolymer-1 therapy is presently limited to daily subcutaneous administration. Treatment with copolymer-1 by ingestion or inhalation is disclosed in U.S. Pat. No. 6,214,791, but these routes of administration have not been shown to attain clinical efficacy in human patients.

Efficacy

Evidence supporting the effectiveness of glatiramer acetate in decreasing the frequency of relapses in patients with Relapsing-Remitting Multiple Sclerosis (RR MS) derives from two placebo-controlled trials, both of which used a glatiramer acetate dose of 20 mg/day. No other dose or dosing regimen has been studied in placebo-controlled trials of RR MS (www.copaxone.com). A comparative trial of the approved 20 mg dose and the 40 mg dose showed no significant difference in efficacy between these doses (The 9006 trial; Cohen J A et al., Neurology (2007) 68 939-944). Various clinical trials in glatiramer acetate are on-going. These include studies with a higher dose of glatiramer acetate (40 mg—the FORTE study); studies in Clinically Isolated Syndrome patients (the PreCISe study) as well as numerous combination and induction protocols, in which glatiramer acetate is given together with or following another active product.

Side Effects

Currently, all specifically approved treatments of multiple sclerosis involve self injection of the active substance. Frequently observed injection-site problems include irritation, hypersensitivity, inflammation, pain and even necrosis (in the case of interferon 1β treatment) and a low level of patient compliance.

Side effects generally include a lump at the injection site (injection site reaction), aches, fever, and chills. These side effects are generally mild in nature. Occasionally a reaction occurs minutes after injection in which there is flushing, shortness in breath, anxiety and rapid heartbeat. These side effects subside within thirty minutes. Over time, a visible dent at the injection site due to the local destruction of fat tissue, known as lipoatrophy, may develop. Therefore, an alternative method of administration is desirable.

More serious side effects have been reported for glatiramer acetate, according to the FDA's prescribing label, these include serious side effects to the body's cardiovascular system, digestive system (including liver), hemic and lymphatic system, musculoskeletal system, nervous system, respiratory system, special senses (in particular the eyes), urogenital system; also reported have been metabolic and nutritional disorders; however a link between glatiramer acetate and these adverse effects has not been definitively established (FDA Copaxone® label).

Depot Systems

The parenteral route by intravenous (IV), intramuscular (IM), or subcutaneous (SC) injection is the most common and effective form of delivery for small as well as large molecular weight drugs. However, pain, discomfort and inconvenience due to needle sticks makes this mode of drug delivery the least preferred by patients. Therefore, any drug delivery technology that can at a minimum reduce the total number of injections is preferred. Such reductions in frequency of drug dosing in practice may be achieved through the use of injectable depot formulations that are capable of releasing drugs in a slow but predictable manner and consequently improve compliance. For most drugs, depending on the dose, it may be possible to reduce the injection frequency from daily to once or twice monthly or even longer (6 months). In addition to improving patient comfort, less frequent injections of drugs in the form of depot formulations smoothes out the plasma concentration-time profile by eliminating the hills and valleys. Such smoothing out of plasma profiles has the potential to not only boost the therapeutic benefit in most cases, but also to reduce any unwanted events, such as immunogenicity etc. often associated with large molecular weight drugs.

Microparticles, implants and gels are the most common forms of biodegradable polymeric devices used in practice for prolonging the release of drugs in the body. Microparticles are suspended in an aqueous media right before injection and one can load as much as 40% solids in suspensions. Implant/rod formulations are delivered to SC/IM tissue with the aid of special needles in the dry state without the need for an aqueous media. This feature of rods/implants allows for higher masses of formulation, as well as drug content to be delivered. Further, in the rods/implants, the initial burst problems are minimized due to much smaller area in implants compared to the microparticles. Besides biodegradable systems, there are non-biodegradable implants and infusion pumps that can be worn outside the body. Non-biodegradable implants require a doctor's visit not only for implanting the device into the SC/IM tissue but also to remove them after the drug release period.

Injectable compositions containing microparticle preparations are particularly susceptible to problems. Microparticle suspensions may contain as much as 40% solids as compared with 0.5-5% solids in other types of injectable suspensions. Further, microparticles used in injectable depot products, range in size up to about 250 μm (average, 60-100 μm), as compared with a particle size of less than 5 μm recommended for IM or SC administration. The higher concentrations of solids, as well as the larger solid particle size require larger size of needle (around 18-21 gauge) for injection. Overall, despite the infrequent uses of larger and uncomfortable needles, patients still prefer less frequently administered dosage forms over everyday drug injections with a smaller needle.

Biodegradable polyesters of poly(lactic acid) (PLA) and copolymers of lactide and glycolide referred to as poly(lactide-co-glycolide) (PLGA) are the most common polymers used in biodegradable dosage forms. PLA is hydrophobic molecule and PLGA degrades faster than PLA because of the presence of more hydrophilic glycolide groups. These biocompatible polymers undergo random, non-enzymatic, hydrolytic cleavage of the ester linkages to form lactic acid and glycolic acid, which are normal metabolic compounds in the body. Resorbable sutures, clips and implants are the earliest applications of these polymers. Southern Research Institute developed the first synthetic, resorbable suture (Dexon®) in 1970. The first patent describing the use of PLGA polymers in a sustained release dosage form appeared in 1973 (U.S. Pat. No. 3,773,919).

Today, PLGA polymers are commercially available from multiple suppliers; Alkermes (Medisorb polymers), Absorbable Polymers International [formerly Birmingham Polymers (a Division of Durect)], Purac and Boehringer Ingelheim. Besides PLGA and PLA, natural cellulosic polymers such as starch, starch derivatives, dextran and non-PLGA synthetic polymers are also being explored as biodegradable polymers in such systems.

At present no long acting dosage forms of glatiramer acetate are available. This is a huge unmet medical need, as these formulations would be extremely beneficial to many patients, particularly to those with neurological symptoms or physical disabilities.

SUMMARY OF THE INVENTION

The present invention provides long acting parenteral pharmaceutical compositions comprising a therapeutically effective amount of a pharmaceutically acceptable salt of glatiramer, e.g., glatiramer acetate. In particular, the present invention provides a long acting pharmaceutical composition comprising a therapeutically effective amount of glatiramer salt in a depot form, suitable for parenteral administration at a medically acceptable location in a subject in need thereof. The present invention further provides a method of treating multiple sclerosis, comprising the parenteral administration or implantation of a composition comprising a therapeutically effective amount of a pharmaceutically acceptable salt of glatiramer, preferably glatiramer acetate.

Unexpectedly it has now been discovered that the long acting pharmaceutical compositions according to the principles of the present invention provide equal or superior therapeutic efficacy to the commercially available daily injectable dosage forms, with reduced incidence and/or severity of side effects at the local and/or systemic levels.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to other embodiments, the glatiramer acetate or other pharmaceutically acceptable salt of glatiramer comprises about 15 to about 100 amino acids.

According to certain embodiments, the implantable depot is suitable for subcutaneous or intramuscular implantation.

According to alternative embodiments, the long acting parenteral pharmaceutical composition comprises a pharmaceutically acceptable biodegradable or non-biodegradable carrier for glatiramer salts such as glatiramer acetate.

According to some embodiments, the carrier is selected from PLGA, PLA, PGA, polycaprolactone, polyhydroxybutyrate, polyorthoesters, polyalkaneanhydrides, gelatin, collagen, oxidized cellulose, and polyphosphazene. Each possibility represents a separate embodiment of the invention.

According to particular embodiments, the long acting pharmaceutical compositions of the present invention are in the form of microparticles prepared by a water-in oil-in water double emulsification process. In currently preferred embodiments, the long acting pharmaceutical compositions of the present invention comprise an internal aqueous phase comprising a therapeutically effective amount of a pharmaceutically acceptable salt of glatiramer, a water immiscible polymeric phase comprising a carrier selected from a biodegradable and a non-biodegradable polymer, and an external aqueous phase. In other currently preferred embodiments, the water immiscible polymeric phase comprises a biodegradable polymer selected from PLA and PLGA. Each possibility represents a separate embodiment of the invention. In additional embodiments, the external aqueous phase comprises a surfactant selected from polyvinyl alcohol (PVA), polysorbate, polyethylene oxide-polypropylene oxide block copolymers and cellulose esters. Each possibility represents a separate embodiment of the invention.

The present invention encompasses the use of glatiramer acetate or any other pharmaceutically acceptable salt of glatiramer in depot form suitable for implantation into an individual in need thereof for treating multiple sclerosis.

The present invention further encompasses the use of the implantable depot of glatiramer acetate suitable for providing prolonged release or prolonged action of glatiramer in a subject.

Within the scope of the present invention is a pharmaceutically acceptable salt of glatiramer in depot form suitable for use in the treatment of multiple sclerosis or in providing prolonged release or prolonged action of glatiramer in a subject.

The invention also encompasses the combination of glatiramer acetate with at least one additional drug, preferably, an immunosuppressant, particularly fingolimod.

According to some embodiments, the long acting pharmaceutical composition is suitable for a dosing schedule from once weekly to once in every 6 months.

According to particular embodiments, the composition is suitable for dosing from once every 2 weeks to once monthly.

According to some embodiments, the long acting compositions comprise a dose between 20-750 mg of glatiramer acetate per injection.

Specific examples of the long acting compositions will include biodegradable or non-biodegradable microspheres, implants of any suitable geometric shape, implantable rods, implantable capsules, implantable rings, prolonged release gels and erodible matrices. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
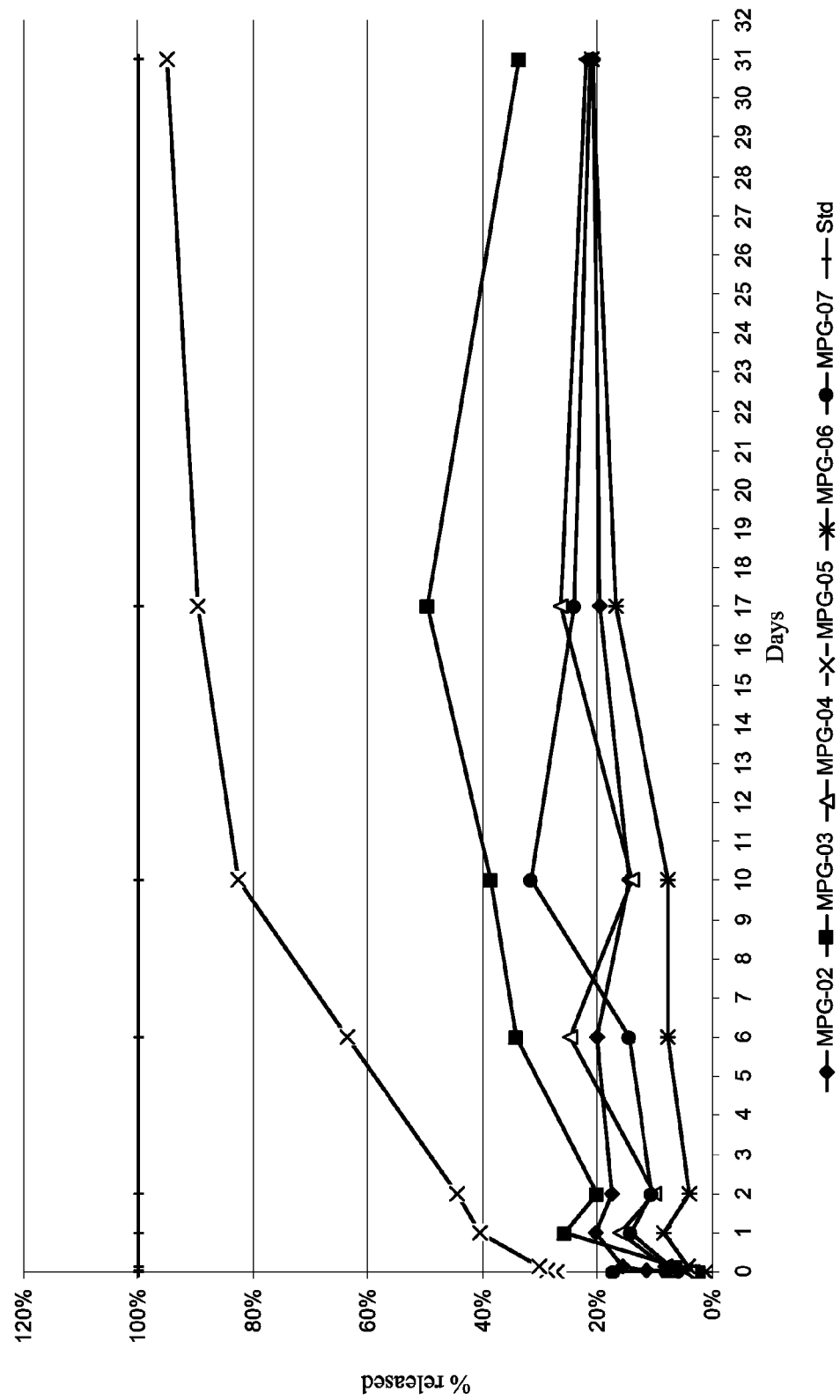
FIG. 1. Release of glatiramer acetate from PLGA microparticulate formulations MPG-02-07 in PBS at 37° C. Data represented are normalized to standard peptide solution stored in same conditions.

The present invention provides pharmaceutical preparations of pharmaceutically acceptable salts of glatiramer, preferably glatiramer acetate, for sustained release by parenteral administration, which afford equal or superior therapeutic efficacy to the daily injections and thus result in improved patient compliance. In addition to providing the same therapeutic efficacy, the long acting injections or implants reduce the glatiramer side effects (local and/or systemic), resulting from frequent injections.

According to a first aspect, the present invention provides a parenteral pharmaceutical composition comprising a therapeutically effective amount of glatiramer acetate or any other pharmaceutically acceptable salt of glatiramer. The term "parenteral" as used herein refers to routs selected from subcutaneous (SC), intravenous (IV), intramuscular (IM), intradermal (ID), intraperitoneal (IP) and the like. Each possibility represents a separate embodiment of the invention. The term "therapeutically effective amount" as used herein is intended to qualify the amount of copolymer that will achieve the goal of alleviation of the symptoms of multiple sclerosis. Suitable doses include, but are not limited to, 20-750 mg for each dosage form. However, it is understood that the amount of the copolymer administered will be determined by a physician, according to various parameters including the chosen route of administration, the age, weight, and the severity of the patient's symptoms. According to various embodiments of the present invention, the therapeutically effective amount of the at least one copolymer ranges from about 1 mg to about 500 mg/day. Alternatively, such therapeutically effective amounts of the at least one copolymer are from about 20 mg to about 100 mg/day.

In another aspect, the present invention provides a long acting pharmaceutical composition comprising a therapeutically effective amount of glatiramer acetate or any other pharmaceutically acceptable salt of glatiramer in a depot form suitable for administration at a medically acceptable location in a subject in need thereof The term "long acting" as used herein refers to a composition which provides prolonged, sustained or extended release of the glatiramer salt to the general systemic circulation of a subject or to local sites of action in a subject. This term may further refer to a composition which provides prolonged, sustained or extended duration of action (pharmacokinetics) of the glatiramer salt in a subject. In particular, the long acting pharmaceutical compositions of the present invention provide a dosing regimen which ranges from once weekly to once every 6 months. According to currently more preferable embodiments, the dosing regimen ranges from once a week, twice monthly (approximately once in every 2 weeks) to once monthly. Depending on the duration of action required, each depot or implantable device of the present invention will typically contain between about 20 and 750 mg of the active ingredient, designed to be released over a period ranging from a couple of weeks to a number of months.

In some embodiments, the depot formulations of the present invention include, but are not limited to, suspensions of glatiramer or a pharmaceutically acceptable salt thereof in water, oil or wax phase; poorly soluble polyelectrolyte complexes of glatiramer or a pharmaceutically acceptable salt thereof; "in-situ" gel-forming matrices based on the combination of water-miscible solvent with glatiramer or a pharmaceutically acceptable salt thereof; and biodegradable polymeric microparticles with incorporated glatiramer or a pharmaceutically acceptable salt thereof. Each possibility represents a separate embodiment of the invention. In particular, the compositions of the present invention are in the form of injectable microparticles wherein the glatiramer or pharmaceutically acceptable salt thereof is entrapped in a biodegradable or non-biodegradable carrier. The microparticulate compositions of the present invention may comprise a water-in oil-in water double emulsion. Within the scope of the present invention is a microparticulate composition comprising an internal aqueous phase comprising glatiramer or any pharmaceutically acceptable salt thereof, an oil phase or water-immiscible phase comprising a biodegradable or non-biodegradable polymer and an external aqueous phase. The external aqueous phase may further comprise a surfactant, preferably polyvinyl alcohol (PVA), polysorbate, polyethylene oxide-polypropylene oxide block copolymers or cellulose esters. The terms "oil phase" and "water-immiscible phase" may be used interchangeably herein.

The present invention further provides a method of treating multiple sclerosis by parenteral administration of a long acting pharmaceutical composition comprising a therapeutically effective amount of glatiramer acetate or any other pharmaceutically acceptable salt of glatiramer to a subject in need thereof. Within the scope of the present invention is a method of treating multiple sclerosis, by administration into an individual in need thereof, glatiramer acetate or any other pharmaceutically acceptable salt of glatiramer in a depot form. The term "treating" as used herein refers to suppression or alleviation of symptoms after the onset of multiple sclerosis. Common symptoms after the onset of multiple sclerosis include, but are not limited to, reduced or loss of vision, stumbling and uneven gait, slurred speech, as well as urinary frequency and incontinence. In addition, multiple sclerosis can cause mood changes and depression, muscle spasms and severe paralysis. The "subject" to which the drug is administered is a mammal, preferably, but not limited to, a human. The term "multiple sclerosis" as used herein refers to an auto-immune disease of the central nervous system which is accompanied by one or more of the symptoms described hereinabove.

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 4,700-11,000 daltons (FDA Copaxone® label) and the number of amino acid ranges between about 15 to about 100 amino acids. The term also refers to chemical derivatives and analogues of the compound. Typically the compound is prepared and characterized as specified in any of U.S. Pat. Nos. 5,981,589; 6,054,430; 6,342,476; 6,362,161; 6,620,847; and 6,939,539, the contents of each of these references are hereby incorporated in their entirety.

In some embodiments, the composition may comprise any other pharmaceutically acceptable salt of glatiramer including, but not limited to, sulfate, pyrosulfate, bisulfate, sulfite, bisulfate, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Each possibility represents a separate embodiment of the invention.

The copolymers can be made by any procedure available to one of skill in the art. For example, the copolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example, dicyclohexylcarbodiimide, can be used to facilitate the formation of the peptide bond.

Blocking groups can be used to protect functional groups, such as the side chain moieties and some of the amino or carboxyl groups against undesired side reactions. The process disclosed in U.S. Pat. No. 3,849,550, the contents of which are hereby incorporated by reference in its entirety, can be used for preparing the copolymers of the invention. For example, the N-carboxyanhydrides of tyrosine, alanine, γ-benzyl glutamate and N, ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by one molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. U.S. Pat. Nos. 6,620,847; 6,362,161; 6,342,476; 6,054,430; 6,048,898 and 5,981,589, the content of which are hereby incorporated by reference in their entirety, disclose improved methods for preparing glatiramer acetate (Cop-1). For purposes of this application, the terms "ambient temperature" and "room temperature" typically means a temperature ranging from about 20° C. to about 26° C.

The molecular weight of the copolymers can be adjusted during polypeptide synthesis or after the polymers have been made. To adjust the molecular weight during polypeptide synthesis, the synthetic conditions or the amounts of amino acids are adjusted so that synthesis stops when the polypeptide reaches the approximate desired length. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the copolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by the test reaction. The trifluoroacetyl-polypeptide with the desired molecular weight profile is then further treated with an aqueous piperidine solution to form a deprotected polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In certain embodiments, the dosage forms include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy} methane), CPM; poly(p-{carboxyphenoxy} propane), CPP; poly(p-{carboxyphenoxy} hexane)s CPH; polyamines, polyurethanes, polyesteramides, polyorthoesters {CHDM: cis/trans- cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly (malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphoshazene and the like. Each possibility represents a separate embodiment.

Currently preferred biodegradable polymer is a lactic acid-based polymer, more preferably polylactide, or poly (D,L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably 100:0 to about 10:90 and has an average molecular weight of from about 1,000 to 200,000 daltons. However, it is understood that the amount of biodegradable polymer is determined by parameters such as the duration of use and the like.

The compositions of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, α-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The compositions of the present invention can be prepared by any manner known in the art. Currently preferred is the incorporation of the glatiramer or salt thereof copolymer into a colloidal delivery system, e.g., biodegradable microparticles, thus allowing release retardation by diffusion through polymeric walls of the particle and by polymer degradation in water media or biological fluids in the body. The compositions of the present invention can be prepared in the form of injectable microparticles by a process known as the "double emulsification". Briefly, the concentrated solution of the water-soluble copolymer is dispersed in a solution of the biodegradable or non-biodegradable polymer in water-immiscible volatile organic solvent (e.g. methylene chloride, chloroform and the like). The thus obtained "water-in-oil" (w/o) emulsion is then dispersed in a continuous external water phase containing surfactant (e.g. polyvinyl alcohol—PVA, polysorbates, polyethylene oxide-polypropylene oxide block copolymers, cellulose esters and the like) to form "water-in oil-in water (w/o/w) double emulsion" droplets. After evaporation of the organic solvent, the microparticles solidify and are collected by filtration or centrifugation. The collected microparticles (MPs) are washed with purified water to eliminate most of the surfactant and non-bonded peptide and centrifugated again. The washed MPs are collected and lyophilized without additives or with the addition of cryoprotectant (mannitol) to facilitate their subsequent reconstitution.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to 100 μm.

The depot systems of the present invention encompass any forms known to a person of skill in the art. Suitable forms include, but are not limited to, biodegradable or non biodegradable microspheres, implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687, the content of which is hereby incorporated in its entirety. Implantable rods can be prepared as is known in the art using suitable micro-extruders.

According to the principles of the present invention, the long acting pharmaceutical compositions of the present invention provide equal or superior therapeutic efficacy to the commercially available daily injectable dosage forms, with reduced incidence of side effects and with reduced severity of side effects at the local and/or systemic level. In some embodiments, the compositions of the present invention provide prolonged release or prolonged action of glatiramer in a subject as compared to a substantially similar dose of an immediate release formulation of glatiramer acetate.

Encompassed by the present invention is a combination therapy of glatiramer acetate or any other pharmaceutically acceptable salt of glatiramer with at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5): 1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4,-tetrahydro-7-morpholin-yl-2,3-dioxo-6-(trifluoromethyl)quinoxalin-i-yl]methylphosphonate, 1-(4-aminophenyl)-4-methyl-7,8-methylene-dioxy-5H-2,3-benzodiazepine, or (−)1-(4-aminophenyl)-4-methyl-7,8-methylene-dioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins, e.g. natalizumab (ANTEGREN®); anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl] propane-1,3-diol; fingolimod) belonging to the class of immunosuppressants.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

General Preparation Methods

PLGA Based Injectable Depot Particles

Microparticles were prepared by solvent extraction/evaporation method (single emulsion). A solution of 50:50, dichloromethane/ethanol containing 250 mg PLGA and 200 mg glatiramer acetate was slowly poured into an aqueous solution (200 ml) containing 2% PVA and emulsified using a mechanical stirrer (300 rpm) at 25° C. The organic solvent was evaporated under stirring (100 rpm) for 2 h. The thus formed microparticles were collected by centrifugation and washed with distilled water to remove excessive emulsifier. The final suspension was then freeze-dried to obtain a fine powder.

Polycaprolactone Based Injectable Depot Particles

Microparticles were prepared by solvent extraction/evaporation method (single emulsion). A solution of 70:30, dichloromethane/acetone containing 500 mg polycaprolactone and 200 mg glatiramer acetate was slowly poured into an aqueous solution (200 ml) containing 2% PVA, 1% Tween 80 and emulsified using mechanical stirrer (500 rpm) at 25° C. The organic solvent was evaporated under stirring (300 rpm) for 4 h. The formed microparticles were collected by centrifugation and washed with distilled water to remove excessive emulsifiers. The final suspension was then freeze dried to obtain a fine powder.

PLGA Based Implant-Rods

PLGA based biodegradable rod shaped implants, 20 mm in length and 2 mm in diameter, were prepared by solvent extraction/evaporation method. A solution of 50:50, dichloromethane/ethanol containing 250 mg PLGA and 200 mg glatiramer acetate was slowly poured into special rod shaped mold. The organic solvent was evaporated in vacuum oven during 12 hrs at room temperature. Alternatively the rod shaped implant was prepared by extrusion of the mixture of 250 mg PLGA and 200 mg of glatiramer at 85-90° C., using a screw type extruder (Microtruder Rancastle RCP-0250 or similar), with die diameter 0.8 or 1.0 mm.

Example 2

Analytical Method—Assay of Glatiramer Acetate

Equipment
  Spectrophotometer
  Analytical balance, capable of accurately weighing to 0.01 mg
Materials and Reagents
  Glatiramer acetate 83% as a reference standard
  2,4,6-trinitrobenzenesulfonic acid (TNBS, picrylsulfonic acid, 170.5 mM) 5% in MeOH
  0.1 M borate buffer pH 9.3 (sodium tetraborate decahydrate MW 381.37)
  water, purified
  volumetric pipettes for 0.5, 1.0, 2.0 and 7.0 mL
  miscellaneous glassware.
Preparations
  Preparation of Glatiramer Stock Solution 400 ng/mL
  4.8 mg of glatiramer acetate (potency 83% as base for reference standard) were weighed into a 10 ml volumetric flask. Approximately 7 ml of 0.1M borate buffer were added to afford dissolution of the glatiramer acetate in ultrasonic bath. The solution was further diluted with 0.1M borate buffer to obtain glatiramer stock solution 400 µg/ml (as base).
  Preparation of 0.25% TNBS Working Solution
  Prior to the use, 5% stock solution of TNBS was diluted with water (20 times; e.g. 50 µl and 950 µl of water) to obtain 0.25% TNBS working solution.
  Calibration Curve Standards Preparation
  Eight glatiramer calibration standard solutions (cSTD; 4 ml each) were prepared according to Table 1.

TABLE 1

Standard solutions of glatiramer acetate

| cSTD # | Concentration of glatiramer µg/ml (as base) | Volume of glatiramer stock solution (ml) | Volume of glatiramer Std 3 (ml) | Volume of 0.1M Borate buffer (ml) |
|---|---|---|---|---|
| Std 0 | 0 | | — | 4 |
| Std 1 | 2 | | 0.4 | 3.6 |
| Std 2 | 10 | | 2 | 2 |
| Std 3 | 20 | 0.2 | | 3.8 |
| Std 4 | 50 | 0.5 | | 3.5 |
| Std 5 | 100 | 1 | | 3 |
| Std 6 | 200 | 2 | | 2 |
| Std 7 | 400 | 4 | | — |

Optical Density Measurement 1.0 ml of each glatiramer calibration standard solutions, samples (in duplicate) and reagent blank (0.1M borate buffer) were transferred into 1.5 ml polypropylene centrifuge tube, to which 50 µl of 0.25% TNBS working solution was added. The solution was thoroughly mixed and kept at room temperature for 30 minutes. The optical densities of each of the obtained solutions were read at 420 nm and 700 nm and the difference of these densities were calculated to avoid error due to light dispersion in colloidal systems. A calibration curve for the selected range of concentrations was calculated.

Acceptance Criteria

The difference between results for duplicate sample preparations was NMT 5%, calculated by following equation:

$$D = \frac{(Rsp11 - Rsp12) \times 2}{Rsp11 + Rsp12} \times 100,$$

in which Rsp11 is the result obtained for sample 1 and Rsp12 is the result obtained for sample 2.

Example 3

Preparation of PLGA Microparticles Loaded with Glatiramer Acetate

External (continuous) water phase: 30 ml of 0.75% NaCl solution in purified water, further containing 0.5% partially hydrolyzed (87-89%) polyvinyl alcohol (PVA) as a surfactant, 0.2% polysorbate-80 (Tween-80) for MPG-10 and 2% PVA for blank MP preparation.

Internal water phase (for peptide solution): 150-200 µl of purified water per 25-30 mg of glatiramer acetate. The glatiramer acetate was dissolved in water using an ultrasonic bath.

Organic polymeric solution (oil phase): 165-300 mg of PLGA in 2-5 mL of methylene chloride. Optionally, a counter-ion was further dissolved or dispersed in the organic phase.

Preparation Proceedings

Water in oil (w/o) emulsion preparation: Internal water phase, containing dissolved glatiramer acetate, was mixed directly in the test tube with the oil phase containing PLGA solution in $CH_2Cl_2$. The mixture was thoroughly shaken and treated with ultrasonic indenter (titanium tip, max. power 120 watt, working power 10-15%, 3-5 cycles of 5 seconds). Cooling was optionally applied using ice or ice water to avoid boiling of methylene chloride.

Double emulsion (w/o/w) preparation: The thus obtained w/o emulsion of the glatiramer acetate solution in polymeric PLGA organic solution, was further treated with high shear mixer (small mixer, VDI-12, shaft diameter 10 mm, and bigger mixer, OMNI-1100, shaft diameter 18 mm) at various speeds for 30-120 seconds.

Solvent elimination: an open beaker with the thus formed double emulsion was placed on the magnetic plate stirrer and stirred for 3-4 hours at room temperature in a fume hood until all methylene chloride evaporated and the microparticles had solidified.

Centrifugation of microparticles: The suspension of solidified microparticles was centrifugated at 2000-5000 g for 10 minutes, the supernatant was transferred into a separate vessel and analyzed for glatiramer acetate content to estimate the peptide incorporation and binding.

Washing of microparticles: the sedimented microparticles from the above described procedure were suspended in 10 ml of purified water using vortex and an ultrasonic bath and shaken or sonicated for 2-3 minutes. The suspension of the microparticles was centrifuged again at 2000-5000 g for 10 minutes, the supernatant was transferred to a separate vessel and analyzed for glatiramer acetate content.

Lyophilization: The washed precipitate of microparticles was re-suspended in 3-5 ml of purified water or 5% mannitol, transferred to 10 ml pre-weighed glass vials, frozen using lyophilizer plate set at −37-43° C. and lyophilized (main drying for 16-48 hours at −20° C. and vacuum 0.05 bar, final drying for +12-16 hours at +20° C. and 0.025 bar). Vials after lyophilizing were weighed, closed with bromobutyl rubber stoppers and stored at refrigerator storage conditions until use.

Particle size estimation: particle size of the microparticles was evaluated using light field and phase contrast microscopy (Leutz Orthoplan™, Germany) with objectives 40× and 10× and stage micrometer with range of 1-1000 μm.

All microparticle formulations were prepared using water phase containing 0.75% sodium chloride to increase the external osmotic pressure and to improve the incorporation of the water-soluble charged drug. Blank (empty) microparticles (first experiment) were obtained with 2% PVA as a surfactant, whereas for the preparation of all peptide loaded formulations 0.5% PVA was used.

Compositions and parameters of the preparation process are presented in Tables 2-5.

TABLE 2

PLGA microparticles for sustained release of glatiramer acetate (GA) (formulations 1-4)

|  | MP Blank | MPG-01 | MPG-02 | MPG-03 | MPG-04 |
|---|---|---|---|---|---|
| Internal water phase |  |  |  |  |  |
| GA, mg |  | 17 | 60.25 | 30 | 18.7 |
| GA dry base, mg | 0 | 14.11 | 50.0 | 24.9 | 15.5 |
| Water for GA, μl |  | 100 | 400 | 200 | 100 + 50 μl of 2% PVA |
| Polymer in the oil phase |  |  |  |  |  |
| PLGA RG 502H, mg | 215 | 270 |  |  | 165 |
| PLGA RG 502, mg |  |  | 500 | 220 |  |
| Oil phase |  |  |  |  |  |
| Tocopheryl succinate |  | 100 | 120 | 50 | 65 |
| Methylene chloride | 2 ml (2.3 g) | 4.5 g | 9 g | 3.2 g | 3 g |
| External water phase |  |  |  |  |  |
| PVA (2% or 0.5%) | 23 ml 2% | 65 ml 0.5% | 60 ml 0.5% | 30 ml 0.5% | 30 ml 0.5% |
| NaCl | 0 | 0.5 g | 0.5 g | 0.25 g | 0.25 g |
| Preparation process description (processor, speed set, evaporation duration) | IKA VDI-12 #5 30 sec, evap. overnight RT magnetic stirrer | IKA VDI-12 #5 2 min, evap. overnight RT magnetic stirrer | IKA VDI-12 #5 2 min, evap. overnight RT magnetic stirrer | IKA VDI-12 #5 2 min, evap. 4 hr RT magnetic stirrer | IKA VDI-12 #5 2 min, evap. 4 hr RT magnetic stirrer |
| Microparticles description | spherical MP 10-50 μm smooth surface | spherical MP 5-20 μm porous surface | aggregate MP 10-30 μm porous surface | spherical MP 10-15 μm slightly porous surface | spherical MP 10-15 μm slightly porous surface |
| Binding (association with MPs) |  | 86% | 34% | 61% | 70% |

VWR VDI-12 high shear mixer from IKA Germany with small diameter of the stator (shaft 12 mm) and speed range 8-30,000 rpm was set in position #5 (approx. 24,000 rpm). Short treatment (30 sec) of approx. 10% PLGA solution in methylene chloride in 2% PVA phase was used to prepare blank MP sample, which resulted in smooth spherical microparticles with relatively wide size distribution (10-50 μm). Due to foaming, further process was carried out at lower concentration of surfactant. Homogenization time was also extended (1 or 2 minutes treatment) to obtain a more narrow size distribution.

Due to the presence of internal water phase in the double emulsion, all the microparticles prepared with the glatiramer peptide had visible inclusions and porosity signs either on the MP surface or inside the particle, when observed under optical microscope.

TABLE 3

PLGA microparticles for sustained release of glatiramer acetate (GA) (formulations 5-7)

|  | MPG-05 | MPG-06 | MPG-07 |
|---|---|---|---|
| Internal water phase |  |  |  |
| GA, mg | 30.8 | 20 | 20 |
| GA dry base, mg | 25.6 | 16.6 | 16.6 |
| Water for GA, μl | 100 + 50 PVA 2% | 166 | 175 |
| Polymer in the oil phase |  |  |  |
| PLGA RG 502H, mg | 165 |  |  |
| PLGA RG 502, mg |  | 200 | 250 |

TABLE 3-continued

PLGA microparticles for sustained release of glatiramer acetate (GA) (formulations 5-7)

|  | MPG-05 | MPG-06 | MPG-07 |
|---|---|---|---|
| Oil phase | | | |
| Dicetylphosphate | | 75 | |
| Dimyristoylphosphatidyl glycerol sodium (DMPG Na) | | | 60 |
| Methylene chloride | 2.7 g | 2.5 g | 3.25 g |
| External water phase | | | |
| PVA (0.5%) | 30 ml | 30 ml | 30 ml |
| NaCl | 0.25 g | 0.25 g | 0.25 g |
| Observations and comments | | Flakes formed from DCP and GA | DMPG Na is poorly soluble in $CH_2Cl_2$ |
| Preparation process description (processor, speed set, evaporation duration) | IKA VDI-12 #5 2 min, evaporation 4 hr RT magetic stirrer | IKA VDI-12 #5 2 min, evaporation 4 hr RT magnetic stirrer | IKA VDI-12 #5 2 min, evaporation 4 hr RT magnetic stirrer |
| Microparticles description | spherical MP 10-15 μm slightly porous surface | irregular particles | spherical MP 5-15 μm |
| Binding (association with MPs) | 81% | 76% | 84% |

The formed glatiramer acetate loaded microparticles were centrifugated; the pellet was re-suspended in purified water, washed and repeatedly centrifuged. Supernatant and in some cases washing water were analyzed for glatiramer acetate content. The centrifugated precipitate was re-suspended in purified water or 5% mannitol solution and lyophilized.

TABLE 4

PLGA microparticles for sustained release of glatiramer acetate (GA) (formulations 05R, 08-011 and tocopheryl succinate salt of glatiramer)

|  | MPG-08 | MPG-09 | MPG-10 | MPG-11 | MPG-05R | Tocopheryl succinate salt 1:1 |
|---|---|---|---|---|---|---|
| Internal water phase | | | | | | |
| GA, mg | 30.1 | 30.1 | 30.1 | 30.1 | 30.9 | 30.1 |
| GA dry base, mg | 25.0 | 25.0 | 25.0 | 25.0 | 25.6 | 25.0 |
| Water, μl | 150 | 200 | 200 | 200 | 200 | 200 |
| Polymer | | | | | | |
| PLGA RG 502H, mg | 165 | 165 | | | 165 | |
| PLGA RG-503, mg | | | 165 | 165 | | 0 |
| Oil phase | | | | | | |
| Tocopheryl succinate, mg | 20 | 50 | 20 | 50 | 0 | 10 |
| Methylene chloride | 2.7 g | 2.7 g | 2.7 g | 3.2 g | 3.7 g | 2 g |
| External water phase | | | | | | |
| Surfactant | 30 ml 0.5% PVA | 30 ml 0.5% PVA | 30 ml 0.2% Tw80 | 30 ml 0.5% PVA | 30 ml 0.5% PVA | 20 ml $H_2O$ |
| NaCl | 0.25 g | 0.25 g | 0.25 g | 0.25 g | 0.25 g | — |
| Preparation process description (processor, speed set, evaporation duration) | OMNI GLH #4 1 min, evap. 4 hr RT mag. stirrer | OMNI GLH #4 1 min, evap. 4 hr RT mag. stirrer | OMNI GLH #4 1 min, evap.4 hr RT mag. stirrer | OMNI GLH #4 1 min, evap.4 hr RT mag. stirrer | IKA VDI-12 #5 2 min, evap.4 hr RT mag. stirrer | 22 kHz Titanium indenter sonication 13 W 60 sec |

TABLE 4-continued

PLGA microparticles for sustained release of glatiramer acetate (GA) (formulations 05R, 08-011 and tocopheryl succinate salt of glatiramer)

|  | MPG-08 | MPG-09 | MPG-10 | MPG-11 | MPG-05R | Tocopheryl succinate salt 1:1 |
|---|---|---|---|---|---|---|
| Microparticles description | Spherical MP 2-5 µm smooth | Spherical MP 1-3 µm smooth | Spherical MP 3-5&20 µm smooth | Spherical MP 2-4 µm smooth | Spherical MP 1-10 µm with inclusions | Spherical agglomerate 30-100 µm |
| Binding (association with MPs) | 82% | 87% | 46% | 85% | 93% | 89% |

Formulation of an equimolar complex (salt) of tocopheryl succinate (MW 530, one COOH eq. 265 Dalton) and glatiramer acetate (MW 4,700-11,000, one $NH_2$ eq. ~693 Dalton) was prepared by suspending an aqueous solution of glatiramer in methylene chloride with previously dissolved equimolar amount of tocopheryl succinate with the help of an ultrasonic indenter for 60 seconds (6×10 sec) with ice cooling. After evaporation of the organic solvent and water, the thus formed water insoluble product was collected, washed with purified water and with dry ethanol and used for further investigations without additional purification.

TABLE 5

PLGA microparticles for sustained release of glatiramer acetate (GA) (formulations MPG-12-15)

|  | MPG-12 | MPG-13 | MPG-14 | MPG-15 |
|---|---|---|---|---|
| Internal water phase |  |  |  |  |
| GA, mg | 31.8 | 31.8 | 31.5 | 31.7 |
| GA dry base, mg | 26.4 | 26.4 | 26.1 | 26.3 |
| Water, µl | 200 | 200 | 200 | 200 |
| Polymer in the oil phase |  |  |  |  |
| PLGA RG 502H, mg | 200 | 250 | 300 | 165 |
| Oil phase |  |  |  |  |
| Tocopheryl succinate, mg |  |  |  | 9 |
| Methylene chloride | 2.6 g | 2.7 g | 2.7 g | 2.6 g |
| External water phase |  |  |  |  |
| 0.5% PVA solution | 30 ml | 30 ml | 30 ml | 30 ml |
| NaCl | 0.25 g | 0.25 g | 0.25 g | 0.25 g |
| Preparation process description (processor, speed set, evaporation duration) | IKA VDI-12 #5 (1 min), evaporation 4 hr RT magnetic stirrer | IKA VDI-12 #5 (1 min), evaporation 4 hr RT magnetic stirrer | IKA VDI-12 #5 (1 min), evaporation 4 hr RT magnetic stirrer | IKA VDI-12 #6 20 sec, #5 40 sec, evaporation 4 hr RT magnetic stirrer |
| Microparticles description | spherical particles 10-15 µm with inclusions | spherical particles 10-18 µm with inclusions | spherical particles 10-15 µm with inclusions | spherical particles 6-10 µm with inclusions; aggregates |
| Binding (association with MPs) | 85.4% | 94.9% | 96.4% | 70.9% |
| Burst (release at 1 hour) | 18.9% | 8.5% | 9.5% | 13.6% |
| Amount of GA, released between day 4 and day 11 | 25.6% | 21.0% | 32.7% | 19.6% |

Lyophilization

Microparticulate formulations after centrifugation and washing were lyophilized either "as is", following sediment re-suspension in purified water, or in some cases, with the addition of cryoprotectant (sediment was re-suspended in a 5% mannitol solution). Samples were frozen for 1 hour at −37-43° C. using the lyophilizer plate, and freeze-dried using lyophilizer "Alpha 2-4 LSC" (Christ, Germany) for 24-48 hours at pressure 0.050 mbar and −20° C., final drying at 0.025 mbar and +20° C. for 10-16 hours. In both re-suspension procedures the lyophilized product could be easily reconstituted. The use of mannitol lead to a readily reconstituted product as compared to formulations without the cryoprotectant, but such compositions contained significant amount of ballast material and required more complex calculations to determine the real concentration of the active material.

Example 4

In vitro Release of Glatiramer Acetate from PLGA Microparticles

Equipment
20 ml vials
multi-point magnetic stirrer
Incubator
Pipettors
UV-Vis spectrophotometer Shimadzu 1601
Reagents and plastic/glassware
Test-Articles Formulations MPG-02, 03, 04, 05, 05R, 06, 07, 12, 13, 14, and 15-50 mg of dry lyophilized microparticles.

Formulations MPG-08, 09, 10, and 11—amount corresponding to 50 mg of dry microparticles, lyophilized with 5% mannitol.

Control glatiramer acetate solution 20-50 µg/mL (as base) in PBS with 0.05% sodium azide)

Temperature: 37° C.

In order to evaluate the release of incorporated glatiramer acetate from biodegradable PLGA microparticles loaded with glatiramer acetate (various formulations), the following process had been employed.

Process description: 20 ml of PBS (0.01M phosphate, 0.05% NaN$_3$) pH 7.4 were added to each vial. The vials were placed at 37° C. and stirred with a small magnet. 600 µl samples were centrifugated at 10,000 g for 5 minutes. 500 µl of supernatant were transferred to a 1.5 ml microtube followed by the addition of 500 µl of 0.1M borate buffer (2-fold dilution) and 50 µl TNBS. The resulting composition was torturously mixed and was kept on the bench for 30 minutes. Analysis was performed using TNBS method.

The remaining precipitated particles, re-suspended with 500 µl of fresh PBS (with NaN$_3$), were returned to the vial. Correct calculation for released amount of glatiramer acetate was performed in further release process for 2.5% for each time-point.

The release of the incorporated glatiramer acetate was carried out in tightly closed 20 ml glass vials, using incubator at 37° C., equipped with a multi-point magnetic stirrer. Phosphate buffered saline (PBS) with pH 7.4 was used as a release media.

The release of the glatiramer acetate was tested over a period of 10-32 days.

The equation for the calibration curve in the range 1-200 µg/ml was calculated (Shimadzu UV-1601) as:

$$OD=0.035+0.0132*C(r^2=0.9985)$$

Where OD—optical density (difference at 420 and 700 nm)

C—concentration of glatiramer acetate base, µg/ml

Results of peptide release of formulations MPG01-MPG07 are shown in FIG. 1. The fastest release of the incorporated glatiramer acetate (40% for days 1-10) was obtained in formulation MPG-05, based on low molecular weight PLGA polymer with acidic end groups (Resomer RG 502H) and without hydrophobic counter-ion. Neutral polymer RG 502 with relatively small amount of tocopheryl succinate as a counter-ion (MPG-03) also demonstrated significant release (~30% for days 2-12), but with lower absolute release values. Formulations containing higher amounts of counter-ions showed suppression of the drug release. Without being bound by any theory or mechanism of action, this might be attributed to the high hydrophobicity of the formed complex. Additionally, the preparation of the microparticles with DCP or DMPG was associated with the formation of aggregates and a wide particle size distribution.

The use of a bigger and more powerful high shear mixer OMNI GLH (shaft diameter 20 mm, 5000-30000 rpm instead of VDI-12 (12 mm shaft) leads to a significant decrease in the size of microparticles (formulations 8-11) and increased surface smoothness. Increasing of amount of the organic solvent (MPG-02) caused decreased peptide incorporation into the microparticles. Without being bound by any theory or mechanism of action, this is possibly attributed to the increase of the intermediate o/w/o double emulsion droplet size. Similarly, the use of polysorbate as non-ionic surfactant also negatively affected the drug loading (MPG-10 with 0.2% Tween-80). The addition of hydrophobic counter-ions (tocopheryl succinate, dimyristoylphosphatidylglycerol DMPG, dicetylphosphate DCP) significantly retarded peptide release from the polymeric microparticles in comparison to formulations without counter-ion (MPG-05, MPG-05R). Without being bound by any theory or mechanism of action, the addition of the hydrophobic counter-ions may provide microparticles with compromised properties (MPG-06).

The chemical structure of the polymer used showed a greater impact on the release properties than the molecular weight of the PLGA. Resomers RG 502H and RG 502 (MW about 17,000 Dalton) had very similar diffusion coefficients, but the main factor determining the release of the included peptide form the polymeric matrix was a multi-point ionic interaction between positively charged Lys moieties of glatiramer acetate and carboxylic end groups in PLGA polymer. Neutral Resomer® RG 502 showed a low binding capacity even in the presence of a counter-ion (MPG-02, 03) while neutral Resomer® RG 503 with higher molecular weight demonstrated better binding but very slow release (MPG-10, 11).

Figure 2:
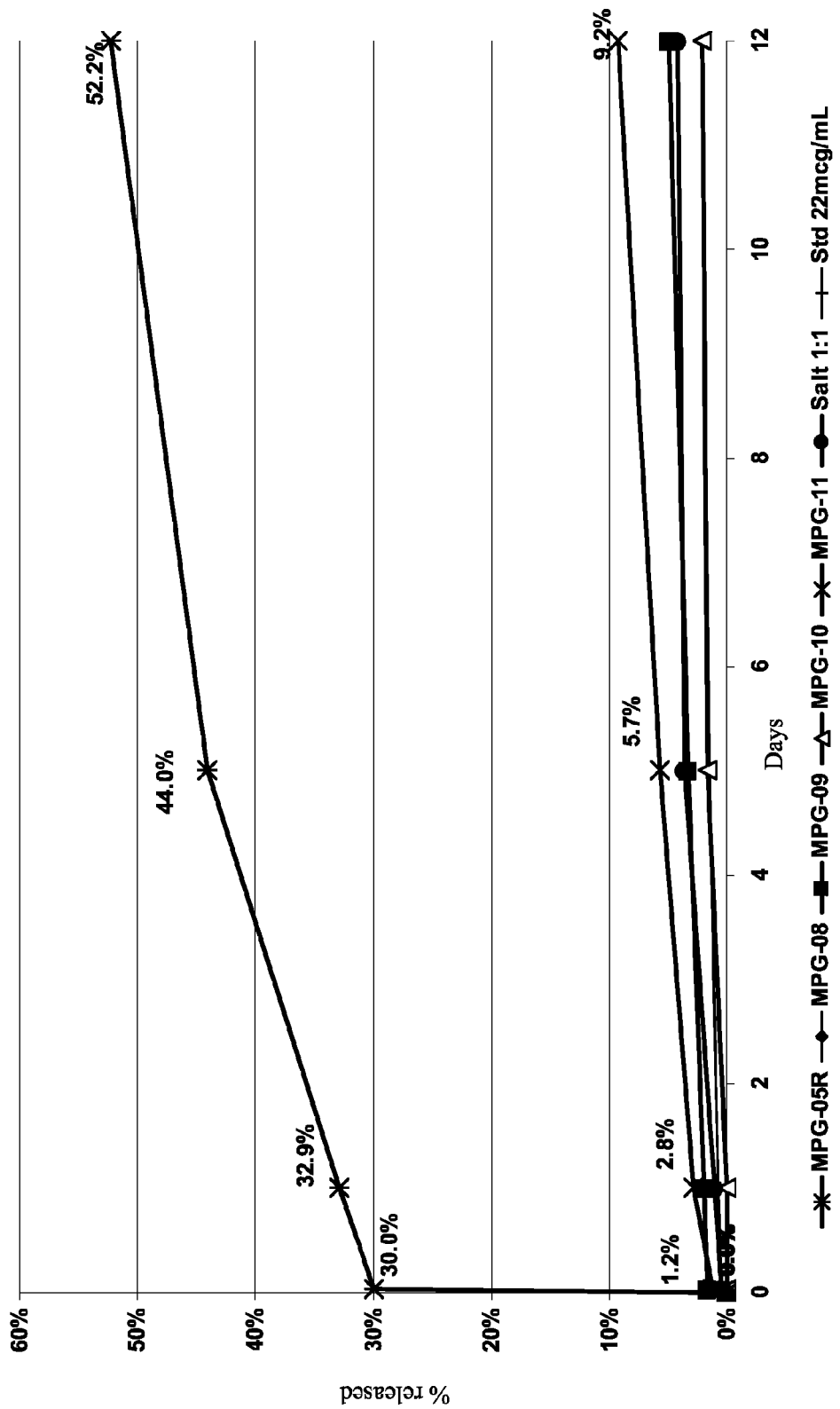
FIG. 2. Release of glatiramer acetate from PLGA microparticulate formulations MPG-05R, 08-11 and tocopheryl succinate salt of glatiramer (1:1) in PBS at 37° C. Data represented are normalized to standard peptide solution stored in same conditions.

Repeated release experiments from separately prepared identical formulations (MPG-05 and MPG-05R) showed reasonably similar behavior and a good reproducibility for such small-scale batches. Formulations of glatiramer acetate with Resomer® RG 502H demonstrated a similar burst effect (~30%), good initial peptide binding and fast drug release (FIG. 2).

Formulation of an equimolar complex (salt) of tocopheryl succinate had a high binding and extremely low water solubility (~5 µg/ml). Without being bound by any theory or mechanism of action, this may be caused by an ionic cross-linking of the diacid (tocopheryl succinate) and the polyamine molecule of the polymer. Release of the polymer from this salt in PBS was extremely slow. For polymeric microparticles, when tocopheryl succinate incorporated into the PLGA matrix, only part of this diacid can interact with the polymer, and for complete release suppression higher amount of tocopheryl succinate is required. So release rate may be regulated by the ratio between the glatiramer and PLGA. The amount of organic solvent used may also be of importance but to a lower extent.

Figure 3:
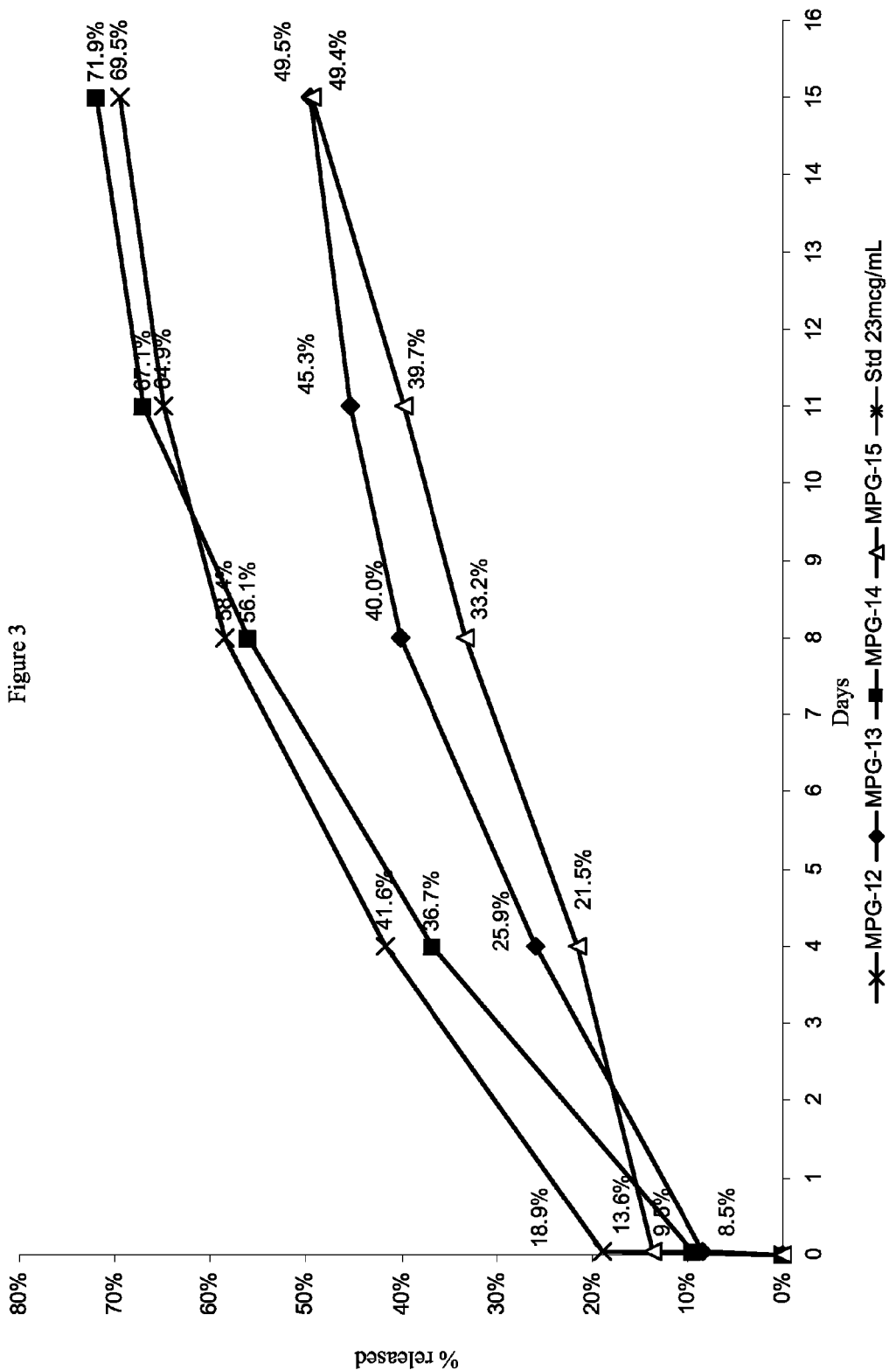
FIG. 3. Release of glatiramer acetate from PLGA microparticulate formulations MPG-12-15 in PBS at 37° C. The data presented are normalized to standard peptide solution stored in same conditions.

Formulations 12-15, based on Resomer® RG 502H with different ratios between the drug and the polymer, showed that the ratio plays an important role in controlling the initial burst effect, the binding level and the release rate. The adjustment of the amount of the PLGA and the peptide as well as the addition of a hydrophobic counter-ion, such as tocopheryl succinate, allows the preparation of microparticulate formulations (MPG-12-15) with high binding, low initial burst and reasonable release rates (FIG. 3).

Example 5

Up Scaling

Lyophilized Samples of Glatiramer Acetate Microparticulate Formulations

MPG-14 SU-1—formulation of MPG-014, was produced using a bigger reaction vessel and a bigger homogenizer (OMNI GLH) at low speed.

Total—13 vials; each vial contained approximately 235 mg of lyophilized formulation with total content of glatiramer acetate of ~18.2 mg per vial, equal to ~75 µg/mg of the lyophilized formulation.

MPG-15 SU-1—formulation of MPG-015, was produced using a bigger reaction vessel and a bigger homogenizer (OMNI GLH) at low speed.

Total—10 vials; each vial contained approximately 145 mg of lyophilized formulation with total content of glatiramer acetate of ~14.9 mg per vial, equal to ~100 µg/mg of the lyophilized formulation.

MPG-14 SU-2—formulation of MPG-014, was produced using the same reaction vessel, the same homogenizer (VDI 12) and the same parameters, process repeated several times. Composition was washed thoroughly to decrease initial burst.

Total—12 vials; each vial contained approximately 88 mg of lyophilized formulation with total content of glatiramer acetate of ~6.3 mg per vial, equal to ~72 µg/mg of the lyophilized formulation.

MPG-15 SU-2—formulation of MPG-015, was produced using the same reaction vessel, the same homogenizer (VDI 12) and the same parameters, process repeated several times. Composition was washed thoroughly to decrease initial burst.

Total—12 vials; each vial contained approximately 55 mg of lyophilized formulation with total content glatiramer acetate of ~5.6 mg per vial, equal to ~100 µg/mg of the lyophilized formulation.

All lyophilized samples were stored in a refrigerator at +4° C. and were reconstituted before use.

Figure 4:
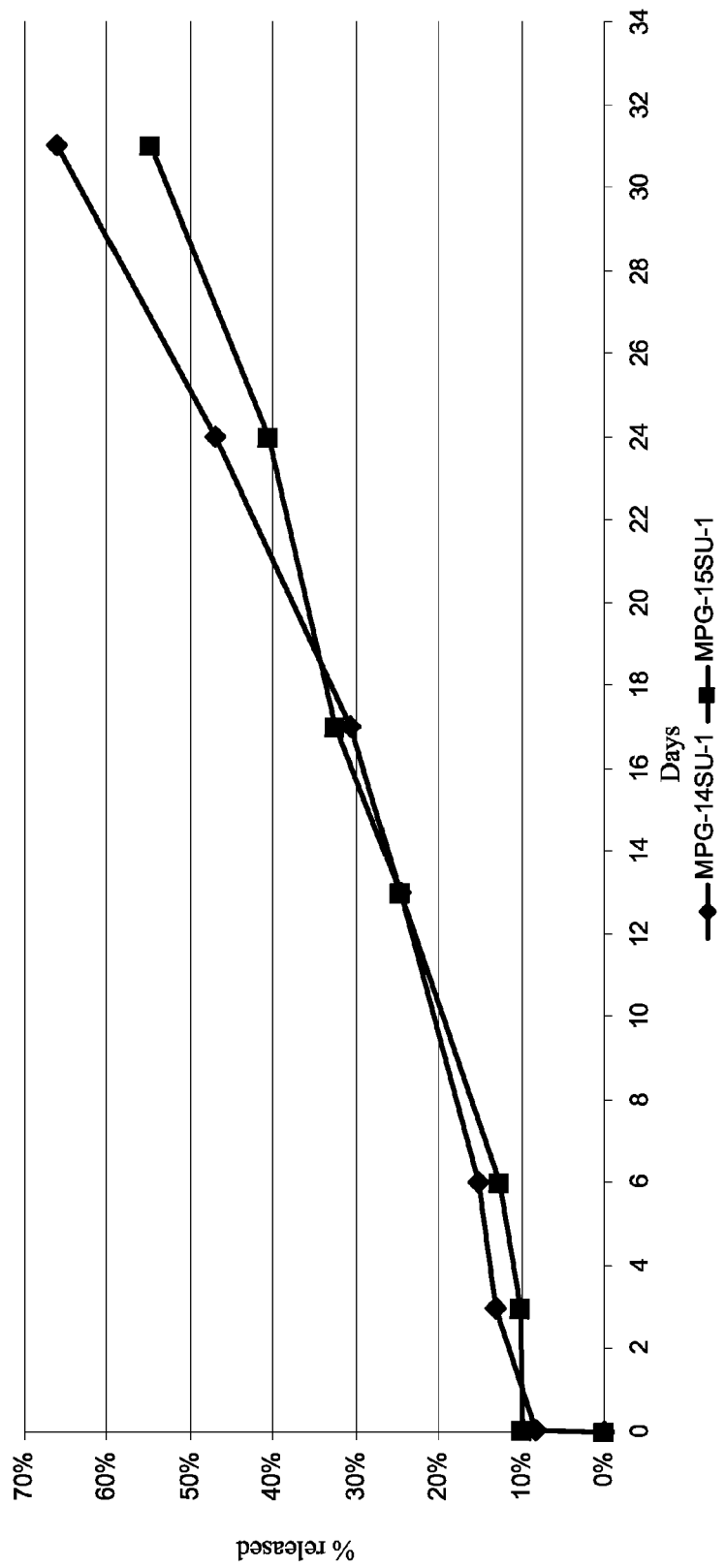
FIG. 4. Release of glatiramer acetate from PLGA microparticulate formulations MPG-14SU-1 and MPG-15SU-1 in vitro in PBS at 37° C., pH 7.4.
Figure 5:
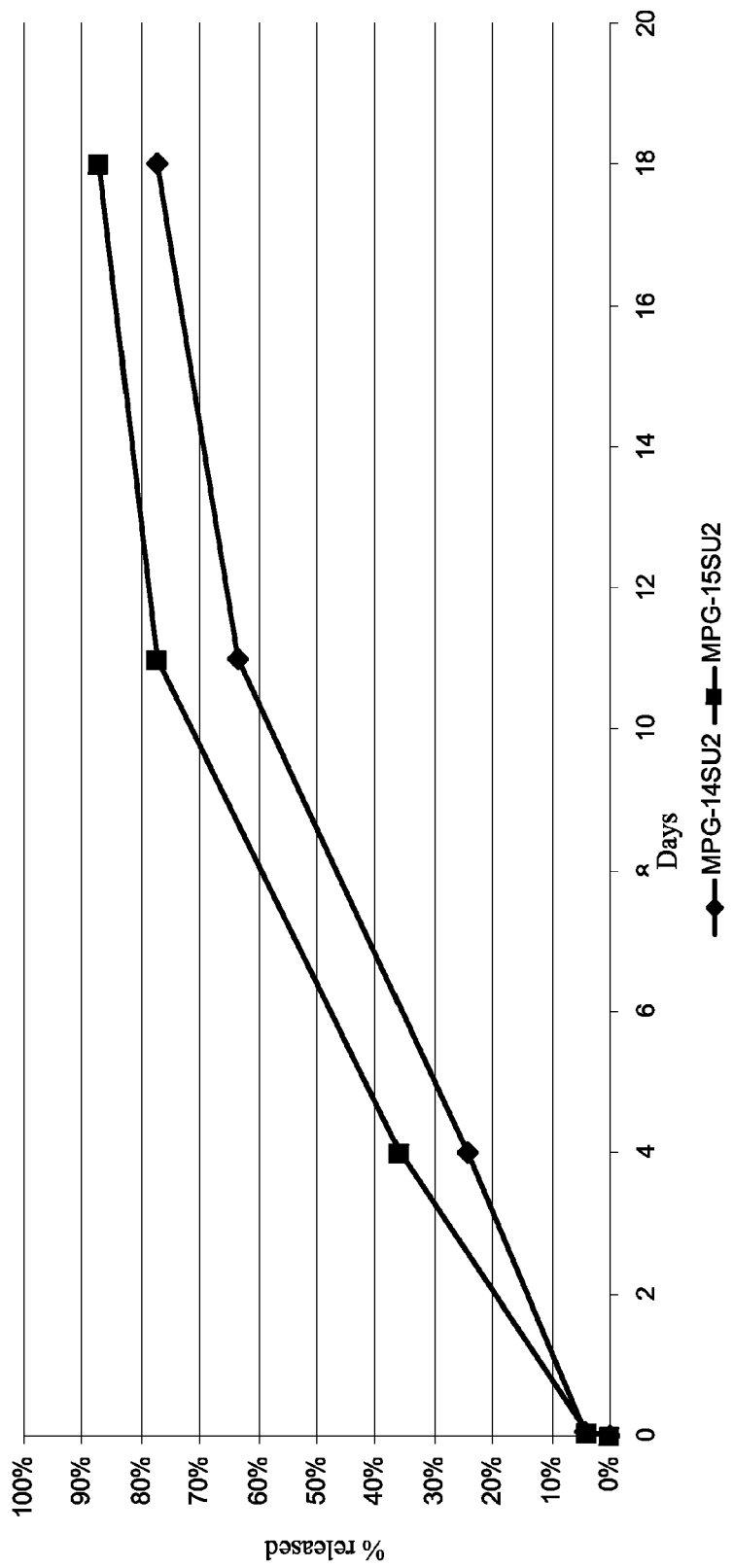
FIG. 5. Release of glatiramer acetate from PLGA microparticulate formulations MPG-14SU-2 and MPG-15SU-2 in vitro in PBS at 37° C., pH 7.4.

The ratio between the formulation and the diluent (glucose solution) was at least 1:5, preferably 1:10 and higher. Vigorous shaking was performed prior to the administration of the reconstituted sample. Release profiles of these formulations are shown in FIGS. 4 and 5.

Thus, the incorporation of the highly water soluble peptide of glatiramer acetate into a biodegradable polymeric microparticles was demonstrated. The microparticles showed good binding of the polymer, reasonable drug loading and reduced initial release burst which can be regulated by employing different compositions and processes of preparation. PLGA microparticles, made of Resomer® 502H and loaded with glatiramer acetate, provide in vitro release of the incorporated peptide with release rate of 3-5% per day for 10-15 days in a stirred aqueous media (phosphate buffered saline, pH 7.4) at 37° C.

Example 6

Experimental Autoimmune Encephalomyelitis (EAE) Model

Experimental autoimmune encephalomyelitis (EAE) is an inflammatory autoimmune demyelinating disease which can be induced in laboratory animals. Such disease has become the standard laboratory model for studying clinical and experimental autoimmune diseases. In fact, numerous articles (e.g., Abramsky et. al., J Neuroimmunol (1982) 2 1 and Bolton et al., J Neurol Sci. (1982) 56 147) note that the similarities of chronic relapsing EAE in animals to multiple sclerosis in humans especially implicates the value of EAE for the study of autoimmune demyelinating diseases such as multiple sclerosis. As such, the EAE test model was employed to establish the activity of the formulations of the present invention against multiple sclerosis.

In the following example, the glatiramer acetate microparticulate formulation designated above as MPG-14 was used and compared to a conventional glatiramer acetate injectable formulation. The conventional formulation is designated herein as "GA", and the microparticulate depot formulation of the invention is designated as "GA-depot". The effect of the two formulations on MOG (myelin-oligodendrocyte-glycoprotein)-induced chronic EAE in C57BL/6 mice was examined according to the procedure described below.

Forty (40) female C57BL/6 mice had been randomly grouped into three (3) groups by body weight in this study; each group consisted of ten (10) mice. The different groups and the dosing regimens are detailed in Table 6. EAE had been induced by injection of emulsion of MOG subcutaneously on the shaved back of the mouse at three sites, followed by an intraperitoneal injection of *Bordetella pertussis* toxin in PBS on Day 0 and 48 hours post MOG immunization. EAE had been assessed by clinical scoring of the mice once daily from Day 0 to Day 14 post immunization. The disease incidence and group mean score had been determined and all treatment groups had been compared to non-treatment control. On Day 14, mice had been terminated.

Test Article Preparation:

GA was dissolved in water-for-injection (WFI). GA depot was suspended in WFI, vortexed and if necessary sonicated for up to 10 minutes without heating, until a homogenous white suspension was obtained, capable to be withdrawn and injected via an adequate needle.

Vehicle Information:

Vehicle 1: saline, 0.9% NaCl in sterile water

Vehicle 2: water for injection (WFI)

Reagents:

MOG 35-55: (GL BiochemCo. Ltd; Shanghai, P.R. China). MOG 35-55 had been dissolved in saline to a concentration of 2 mg/mL.

Complete Freund's adjuvant (CFA) (Cat: F5881; Sigma-Aldrich; St. Louis, Mo., USA). Heat-killed *Mycobacterium tuberculosis* strain H37RA (Cat: 231141; Difco; Detroit, Mich., USA) were added to complete Freund's adjuvant to a final concentration of 4 mg/mL.

*Bordetella pertussis* toxin (PTX): (Cat: P7208; Sigma-Aldrich; St. Louis, Mo., USA)

Using a high-speed homogenizer, the above MOG solution had been emulsified with equal volume of the modified CFA on ice for 30,000 rpm for 1.5 hour.

Animals:

C57BL/6 mice, female, 7-9 weeks, 17-20 g Adaptation: not less than 7 days.

Room: Specific Pathogen Free (SPF) room

Room temperature: 20-26° C.

Room relative humidity: 40-70%

Light cycle: fluorescent light for 12-hour light (08:00-20:00) and 12-hour dark.

Animal hosting: 3-4 mice/cage by treatment group

Food: free access to food (irradiated, Shanghai SLAC Laboratory Animal Co. Ltd., China).

Water: free access to water (municipal tap water filtered by Mol Ultrapure Water System).

Allocation to Treatment Groups:

Animals had been assigned to treatment groups by randomization in Biobook software to achieve similar group mean weight, which provides for control of bias.

divided into 2 doses, each of 5 mg active, administered intramuscularly on day 0 and day 1.

Body weight of all mice had been recorded daily starting from Day 0 to Day 14. EAE development had been assessed by clinically scoring of the mice once daily from Day 0 to Day 14 post immunization according to a scale of 0-5 (0=normal mouse; 1=limp tail or hind limb weakness; 2=limp tail and hind limb weakness; 3=partial hind limb paralysis; 4=complete hind limb paralysis; and 5=moribund state). The incidence, mortality and group mean score had been determined and the treatment groups had been compared to non-treatment control. On Day 14, mice had been terminated.

Mean body weight among the groups had been compared by ANOVA followed by Dunnett's post-Hoc test. Comparisons of the mean clinical score between two groups had been made by Friedman test followed by Dunn's Multiple Comparison Test. Incidence of disease between two groups had been compared among the groups by Peason Chi-squwere test. $p<0.05$ had been considered significant.

Results:

Emulsified MOG induced an inflammatory response as evidenced by clinical manifestations in line with previous data.

TABLE 6

Group and dosing regimen

| Group | Test article | N | Route | Conc. mg/ml | Dosage mL/mice/day | Dosage mg/mice/day | Regimen | Dose on |
|---|---|---|---|---|---|---|---|---|
| 1 | vehicle[a] | 10 | s.c | N/A | 0.2 | N/A | q.d. | day 0-day 9 |
| 2 | GA-depot[b] | 10 | i.m | 335* | 0.2 | 67* | q.d. | day 0, day 1 |
| 3 | GA[b] | 10 | i.m | 25 | 0.2 | 5 | q.d. | day 0, day 1 |

[a]Vehicle is saline

[b]Vehicle is WFI

*GA content is 75 mg/g of "GA-depot" formulated product, i.e. 5 mg/mice/day of GA After anesthetization by isoflurane (2-3%, inhalation), EAE had been induced by injecting 100 μL emulsion subcutaneously into the shaved backs of the mice. *Bordetella pertussis* toxin (200 ng in 200 μL of PBS) had been administered i.p. on the day of immunization (Day 0) and 48 hours thereafter.

Figure 6:
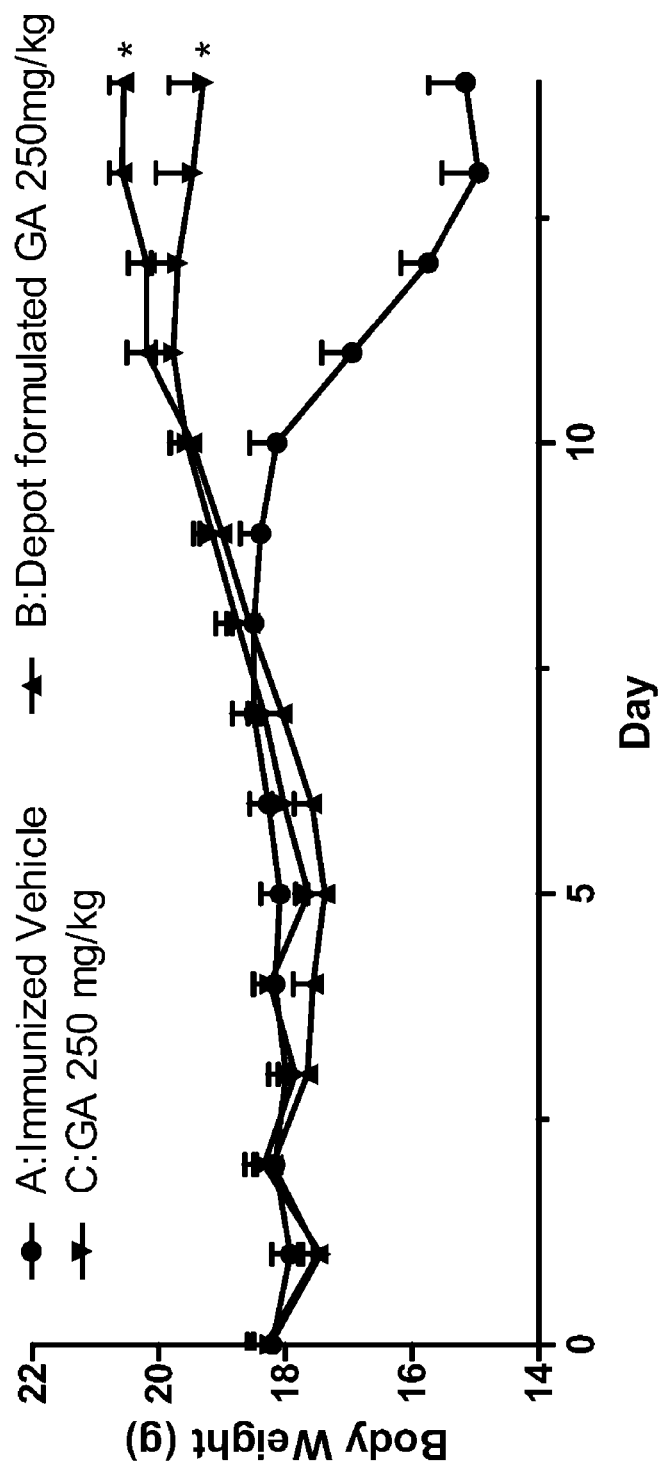
FIG. 6. Effect of glatiramer acetate (GA) depot formulation (B: depot formulated GA 250 mg/kg) versus conventional GA formulation (C: GA 250 mg/kg) and vehicle (A) on body weight in a mouse experimental autoimmune encephalomyelitis (EAE) model. ** $p<0.05$ compared with Immunized-Vehicle by Repeated Measures ANOVA.
Figure 7B:
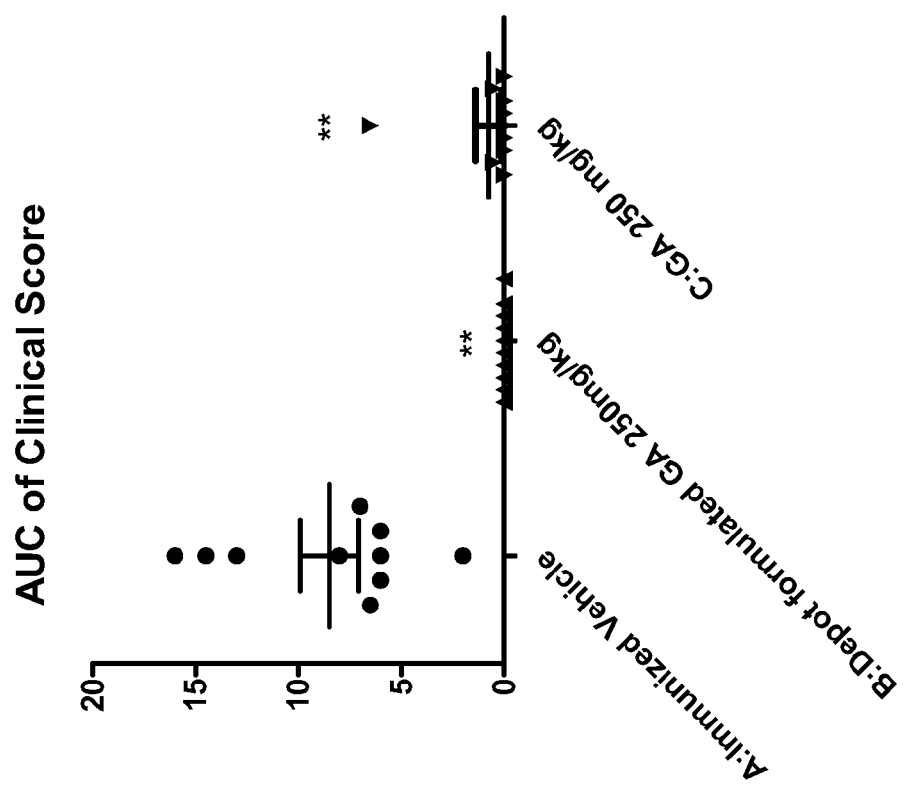
FIG. 7. Effect of glatiramer acetate (GA) depot formulation (B: depot formulated GA 250 mg/kg) versus conventional GA formulation (C: GA 250 mg/kg) and vehicle (A) on clinical score in a mouse EAE model. A) mean clinical score. * $p<0.05$ compared with Immunized Vehicle by Friedman test; B) AUC of clinical score.
Figure 8:
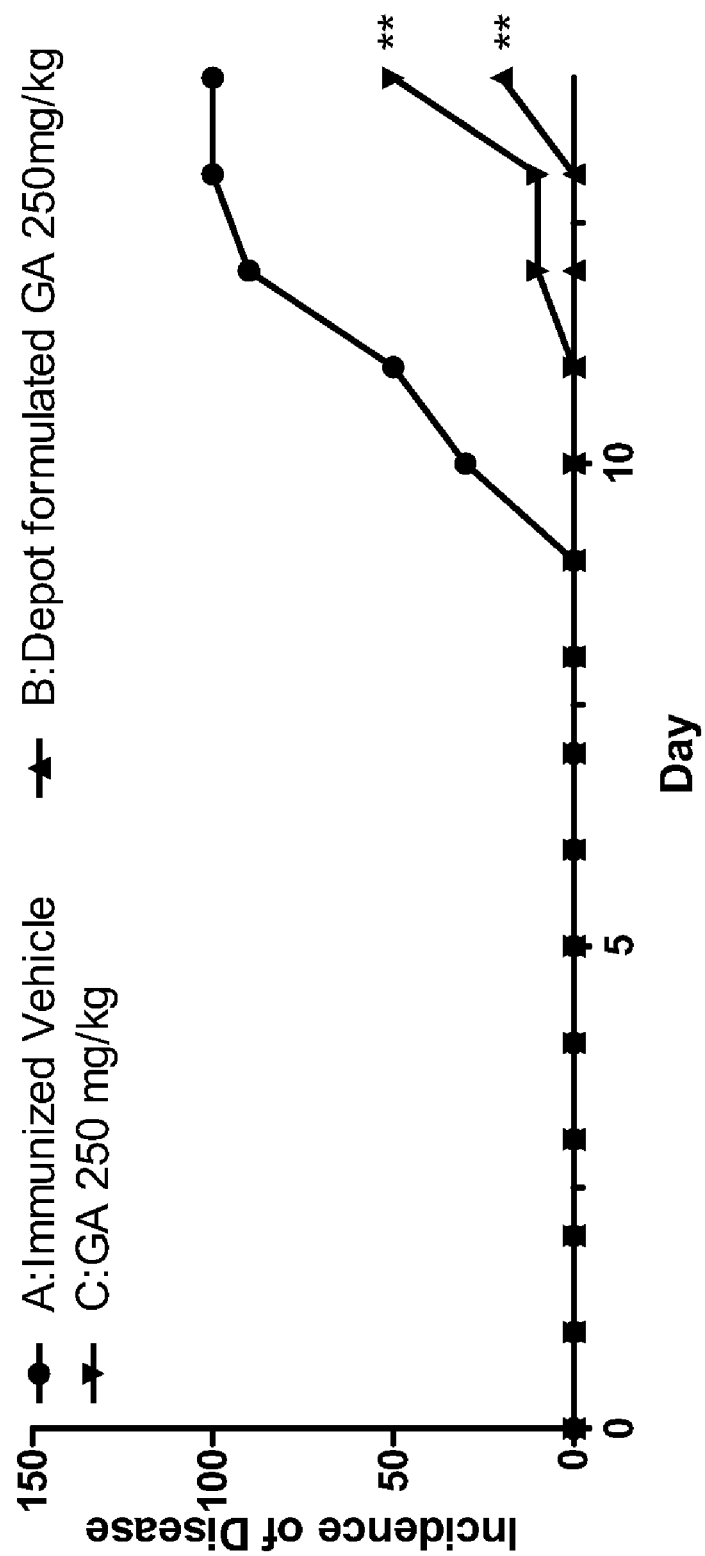
FIG. 8. Effect of glatiramer acetate (GA) depot formulation (B: depot formulated GA 250 mg/kg) versus conventional GA formulation (C: GA 250 mg/kg) and vehicle (A) on incidence of disease in a mouse EAE model. ** $p<0.01$ compared with Immunized Vehicle by Survival Analysis.

Test article or vehicle had been administrated to each group according to the treatment regimes and dosing described in Table 6. Mice in group 1 had been administered subcutaneously, once-daily, for 10 consecutive days. Group 2—a total dose of 10 mg active per mice had been divided into 2 doses, each of 5 mg active ingredient (67 mg formulated product), administered intramuscularly on day 0 and day 1. Group 3—a total dose of 10 mg active ingredient per mice had been As can be seen in FIGS. 6, 7A+B, 8 and in Table 7, throughout the 14 days of the study GA depot completely prevented EAE development—it showed 100% inhibition rate, compared to about 91% inhibition by the conventional formulated GA. GA depot significantly prevented body weight loss and ameliorated clinical symptoms compared to vehicle control, and was more effective compared to GA.

Parameters including maximum score, disease duration and mean day of onset also indicated that GA depot significantly suppressed EAE development, similar to GA, as compared to vehicle.

Thus, GA formulated according to embodiments of the present invention is comparable or better than the conventional formulation when given at the same dosage level.

TABLE 7

| | | | | AUC 0-14 day | | |
|---|---|---|---|---|---|---|
| Group | Maximum score | Disease duration | Mean day of onset | clinical score | Inhibition rate | Mortality |
| 1 (vehicle) | 3.4 ± 0.31 | 3.70 ± 0.33 | 11.3 ± 0.33 | 8.50 ± 1.41 | N/A | 0% |
| 2 (GA-depot) | 0.0 ± 0.00** | 0.0 ± 0.00** | N/A** | 0.0 ± 0.00** | 100% | 0% |
| 3 (GA) | 0.5 ± 0.31 | 0.5 ± 0.31 | N/A | 0.75 ± 0.64 | 91.18% | 0% | disease status summary (0-14 days)

**p < 0.01 statistically significant difference compared with Immunized Vehicle 1 (by Kruskal-Wallis test (for Maximun Score)/One-way ANOVA (for other parameters) followed by Dunn's/Dunnett's Multiple Comparison Test).

Example 7

In Vivo Studies Using the EAE Model

To determine the effect of the formulations of the present invention on the murine model of MS, experimental autoimmune encephalomyelitis (EAE) is performed. 25-hydroxyvitamin $D_3$-1α-hydroxylase knockout mice (1α-OH KO) are maintained on a purified diet containing 0.87% calcium and 1 ng 1,25-$(OH)_2D_3$ (Vit D) for two to three weeks prior to EAE immunization. EAE is induced to mice at six to ten weeks of age, by subcutaneous immunization of 200 μg of the immunodominant peptide to myelin oligodendrocyte glycoproprotein ($MOG_{35-55}$).

The peptide is synthesized using standard 9-fluorenyl-methoxy-carbonyl chemistry. The peptide is dissolved in Freund's complete adjuvant (CFA; Sigma) containing 4 mg/ml of heat-inactivated Mycobacterium tuberculosis H837a.

The mice are examined daily for clinical signs of EAE utilizing the following scoring system: 0, no sign; 1, limp tail; 2, hindlimb weakness; 3, hindlimb paralysis; 4, forelimb paralysis; 5, moribund or death.

Mice that develop clinical signs of EAE with scores ≧2 are treated with the formulation of the present invention which is administered by injection every week/two weeks/once a month at various dosages. Control groups are treated either with placebo or with Gold standard regimen of glatiramer acetate [e.g. PNAS, 2005, vol. 102, no. 52, 19045-19050]. Mice are then weighed and scored daily for symptoms of EAE. Statistical analysis is performed using the two-tailed Fisher exact probability test on incidence rates and the unpaired Student's t-test on all other measurements. Values of P<0.05 are considered statistically significant.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A long acting parenteral pharmaceutical composition comprising a therapeutically effective amount of a pharmaceutically acceptable salt of glatiramer, the composition being in a sustained release depot form which releases a therapeutically effective amount of the pharmaceutically acceptable salt of glatiramer over a period of about one week to about 6 months.

2. The pharmaceutical composition according to claim 1, comprising a therapeutically effective amount of a pharmaceutically acceptable salt of glatiramer in depot form suitable for implantation at a medically acceptable location in a subject in need thereof.

3. The pharmaceutical composition according to claim 1, wherein the pharmaceutically acceptable salt of glatiramer is glatiramer acetate.

4. The pharmaceutical composition according to claim 1, in depot form suitable for subcutaneous or intramuscular implantation.

5. The pharmaceutical composition according to claim 1, wherein the glatiramer comprises L-alanine, L-glutamic acid, L-lysine, and L-tyrosine in molar ratios of about 0.14 glutamic acid, about 0.43 alanine, about 0.10 tyrosine and about 0.33 lysine.

6. The pharmaceutical composition according to claim 1, wherein the glatiramer comprises about 15 to about 100 amino acids.

7. The pharmaceutical composition according to claim 1, further comprising a pharmaceutically acceptable biodegradable or non-biodegradable carrier.

8. The pharmaceutical composition according to claim 7, wherein the carrier is selected from poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene.

9. The pharmaceutical composition according to claim 1 in the form of microparticles prepared by a water-in oil-in water double emulsification process.

10. The pharmaceutical composition according to claim 1 comprising an internal aqueous phase comprising a therapeutically effective amount of a pharmaceutically acceptable salt of glatiramer, a water immiscible polymeric phase comprising a biodegradable or non-biodegradable polymer and an external aqueous phase.

11. The pharmaceutical composition according to claim 10, wherein the water immiscible polymeric phase comprises a biodegradable polymer selected from poly (D,L-lactide) (PLA) and poly (D,L-lactide-co-glycolide) (PLGA).

12. The pharmaceutical composition according to claim 10, wherein the external water phase comprises a surfactant selected form polyvinyl alcohol (PVA), polysorbate, polyethylene oxide-polypropylene oxide block copolymers and cellulose esters.

13. The pharmaceutical composition according to claim 1 in the form of biodegradable microspheres, non-biodegradable microspheres, implants of any suitable geometric shape, implantable rods, implantable capsules, implantable rings, or prolonged release gels or erodible matrices.

14. The pharmaceutical composition according to claim 1, wherein the composition provides equal or superior therapeutic efficacy to the commercially available daily injectable dosage forms of glatiramer acetate, with reduced incidence of side effects and/or with reduced severity of side effects at the local and/or systemic level.

15. The pharmaceutical composition according to claim 14, wherein the composition provides prolonged release or prolonged action of glatiramer in a subject as compared to a substantially similar dose of an immediate release formulation of glatiramer acetate.

16. A method of treating multiple sclerosis comprising the step of parenterally administering to a subject in need thereof a long acting pharmaceutical composition comprising a therapeutically effective amount of a pharmaceutically acceptable salt of glatiramer, the composition being in a sustained release depot form which releases a therapeutically effective amount of the pharmaceutically acceptable salt of glatiramer over a period of about one week to about 6 months.

17. The method according to claim 16, wherein the long acting pharmaceutical composition comprises a therapeutically effective amount of a pharmaceutically acceptable salt of glatiramer in depot form suitable for implantation at a medically acceptable location in a subject in need thereof.

18. The method according to claim 17, comprising the step of implanting into a subject in need thereof the long acting pharmaceutical composition.

19. The method according to claim 16, comprising the step of subcutaneously or intramuscularly administering the pharmaceutical composition.

20. The method according to claim 16, wherein the pharmaceutical composition comprises glatiramer acetate.

21. The method according to claim 20, wherein the glatiramer acetate comprises L-alanine, L-glutamic acid, L-lysine, and L-tyrosine in the molar ratios of about 0.14 glutamic acid, about 0.43 alanine, about 0.10 tyrosine and about 0.33 lysine.

22. The method according to claim 21, wherein the glatiramer comprises about 15 to about 100 amino acids.

23. The method according to claim 16, wherein the pharmaceutical composition further comprises a pharmaceutically acceptable biodegradable or non-biodegradable carrier.

24. The method according to claim 16, wherein the pharmaceutical composition is in the form of microparticles prepared by a water-in oil-in water double emulsification process.

25. The method according to claim 16, wherein the pharmaceutical composition comprises an internal aqueous phase comprising a therapeutically effective amount of a pharmaceutically acceptable salt of glatiramer, a water immiscible polymeric phase comprising a biodegradable or non-biodegradable polymer and an external aqueous phase.

26. The method according to claim 16, wherein the pharmaceutical composition is in the form of biodegradable microspheres, non-biodegradable microspheres, implants of any suitable geometric shape, implantable rods, implantable capsules, or implantable rings, prolonged release gels or erodible matrices.

* * * * *